United States Patent [19]

Pucci et al.

[11] Patent Number: 5,223,431
[45] Date of Patent: Jun. 29, 1993

[54] LEUCONOSTOC DEXTRANICUM NRRL-B-18242

[75] Inventors: Michael J. Pucci, New Britain, Conn.; Blair S. Kunka, Bradenton, Fla.

[73] Assignee: Quest International Flavors & Food Ingredients Company Division of Indopco, Inc., Bridgewater, N.J.

[21] Appl. No.: 393,211

[22] Filed: Aug. 14, 1989

Related U.S. Application Data

[60] Division of Ser. No. 243,677, Sep. 13, 1988, Pat. No. 4,933,191, which is a continuation-in-part of Ser. No. 68,435, Jul. 1, 1987, Pat. No. 4,855,149.

[51] Int. Cl.$^5$ .............................................. C12N 1/20
[52] U.S. Cl. .................................. 435/252.9; 435/103; 435/853
[58] Field of Search ...................... 435/252.9, 103, 853

[56] References Cited

U.S. PATENT DOCUMENTS 2,764,843 10/1956 Peake .

OTHER PUBLICATIONS

Lee, H. C. et al., "Studies on Dextran Production from Surcrose I Production of Dextran by Fermentation", Nat'l Sci. Counc. Monthly, ROC 10 (6), pp. 535-549, 1982.

Zedan, H. H. et al., "Isolation and Identification of Dextran-Producing Microorganisms from Egyptian Sugar Factories", Egypt J. Microbiol., 18, No. 1-2, pp. 191-204, 1983.

Jeanes, A., ACS Symp. Ser. 45: 284-298 (1977).

Preobrazhenskaya, M. E. et al., Biokhimiya i Microbiologiya 10: 539-546 (1974).

Mayeux, J. V. et al., J. Bacteriol. 81: 1009-1011 (1961).

Schwartz, et al., Appl. Environ. Microbiol. 48: 678-679 (1984).

Lawford, G. R. et al., Biotechnol. Bioeng. 21: 1121-1131 (1979).

Cottrell, I. W. et al., Dev. Ind. Microbiol. 19: 117-131 (1978).

Primary Examiner—David M. Naff
Assistant Examiner—M. Knode
Attorney, Agent, or Firm—Ian C. McLeod

[57] ABSTRACT

Leuconostoc dextranicum NRRL-B-18242 which produces a slushy, applesauce-like dextran with a particulate structure is described. The dextran is dried and used in foods and the like.

5 Claims, 1 Drawing Sheet

LEUCONOSTOC DEXTRANICUM NRRL-B-18242

CROSS-REFERENCE TO RELATED APPLICATION

This is a divisional of copending application Ser. No. 07/243,677 filed on Sept. 13, 1988, now U.S. Pat. No. 4,933,191 which is a continuation-in-part of U.S. patent application Ser. No.68,435, filed Jul. 1, 1987, U.S. Pat. No. 4,855,14

BACKGROUND OF THE INVENTION (1) Summary of the Invention

The present invention relates to a novel dextran having a slushy, applesauce-like appearance with a particulate, gel-like structure in crude form produced by *Leuconostoc dextranicum*. In particular the present invention relates to *Leuconostoc dextranicum* NRRL-B-18242 which produces the novel dextran.

(2) Prior Art

Dextrans are glucose polymers synthesized by several genera of bacteria including Streptococcus, Lactobacillus and Leuconostoc (Schwartz, R. D. and E. A. Bodie, *Appl Environ Microbiol.* 48:678-679 (1984); and Lawford, G. R., A. Kligerman and T. Williams, *Biotechnol. Bioeng.* 21:1121-1131 (1979)). Primarily extracellular dextransucrase enzymes synthesize dextrans with molecular weights of $2 \times 10^7$ and higher (Schwartz, R. D. and E. A. Bodie, *Appl. Environ. Microbiol.* 48:678-679 (1984)). The dextrans are primarily alpha 1,6 linked, but may also have alpha 1,4, alpha 1,2, and alpha 1,3 linkages which result in branched polymers of varying water solubilities and other properties (Niinobe, M. and T. Kobayashi, *Nippon Nogeikagaku Kaishi* 46:81-88 (1972)). Dextrans are presently used in a variety of industries, however, uses in foods are nonexistent.

One use of dextrans in the food industry involves gel-filtration to concentrate or recover proteins from liquid wastes such as whey and cereal waste streams (Jeanes, A., *ACS Symp Ser* 45 284-298 (1977)). The dextrans can be used for other non-food purposes such as seed coating as described in U.S. Pat. No. 2,764,843 to Peake.

Dextran synthesis has been widely studied in the genera Leuconostoc, particularly in *L. mesenteroides* (Lawford, G. R., A. Kligerman, and T Williams, *Biotechnol. Bioeng.* 21:1121-1131 (1979); Niinobe, M. and T. Kobayashi, *Nippon Nogeikagaku Kaishi* 46:81-88 (1972); and Preobrazhenskaya, M. E. and N. A. Danilova, *Prikladnaya Biokhimiya i Microbiologiya* 10:539-546 (1974)). Leuconostocs offered several advantages for study First, they are unable to metabolize either dextrans (they contain no dextranases) or sucrose (no invertases or sucrose phosphorylases) (Jeanes, A., *ACS Symp. Ser.* 45:284-298 (1977)). Also, many Leuconostoc strains are prolific producers of sucrose-inducible extracellular dextran sucrases and are, therefore, abundant producers of dextrans. Finally, they are able to metabolize fructose, which is the by-product of dextran synthesis, as an energy source.

Dextrans in aqueous solution are generally characterized as thick and relatively clear or translucent. Usually the upper limit of dextran produced is about fifty percent (50%) by weight based upon the sucrose. The failure to use dextrans in foods is believed to be because of the properties of the food (texture, thickness, mouth feel) are not significantly enhanced by the prior art dextrans.

OBJECTS

It is therefore an object of the present invention to provide a novel dextran which has unique properties which are particularly useful in foods Further it is an object of the present invention to provide a dextran which has a unique slushy, applesauce-like appearance with a particulate, gel-like structure in crude form. Further still, it is an object of the present invention to provide a novel dextran which is produced in high yield based upon the sucrose used to produce the dextran. These and other objects will become increasingly apparent by reference to the following description and the drawings.

GENERAL DESCRIPTION

Figures 1A, 1B:
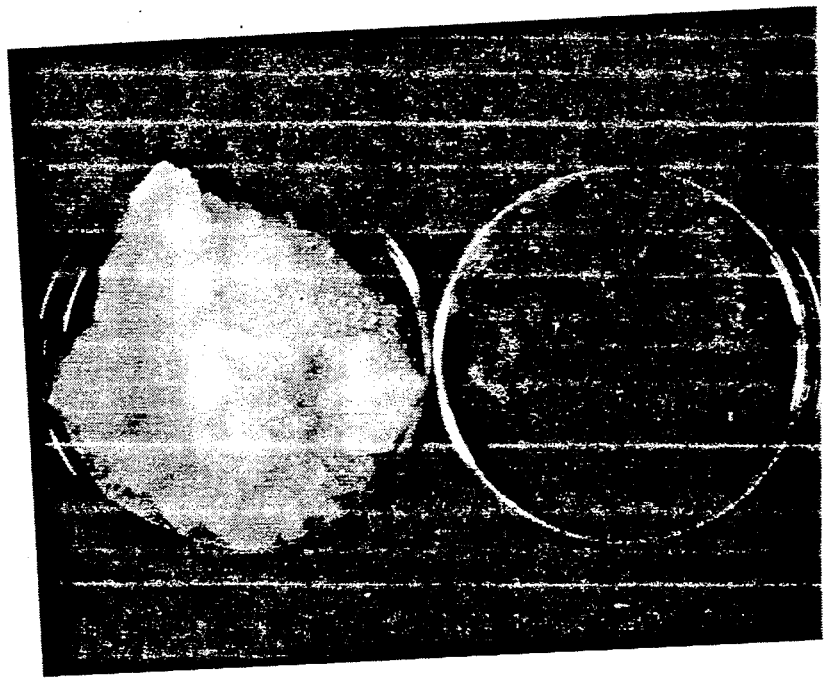
FIGS. 1A and 1B are shown in a single photograph showing the slushy, applesauce-like appearance with the particulate gel-like structure of the crude form of the dextran in FIG. 1A and the clear or translucent thick liquid form of the dextran of the prior art in FIG. 1B.

The present invention relates to a composition which comprises dextran produced by a *Leuconostoc dextranicum*, wherein the dextran is produced in an aqueous sucrose containing growth medium so that the sucrose is substantially depleted and wherein the depleted growth medium containing the dextran has a slushy, applesauce-like appearance with a particulate, gel-like structure as shown in FIG. 1A and wherein the dextran is optionally dried so as to be rehydratable.

The present invention also relates to a composition which comprises dextran produced by a *Leuconostoc dextranicum* and containing 1,6-glucopyranose with branching about every 20 to 30 residues of glucose and having about 5 to 20% by weight fructofuranose.

The present invention further relates to a culture which comprises in admixture: a *Leuconostoc dextranicum* which produces a dextran having a slushy, applesauce-like appearance with a particulate, gel-like dextran structure as shown in FIG. 1A like that produced by *Leuconostoc dextranicum* strain NRRL-B-18242 when grown in an aqueous growth medium containing sucrose so that the sucrose is substantially depleted; and a formulated growth medium for the strain. The composition preferably contains at least about $10^6$ cells per gram. *Leuconostoc dextranicum* NRRL-B-18242 is the preferred strain.

The present invention further relates to a process for producing a novel dextran which comprises providing a sucrose containing growth medium; and inoculating the growth medium with a *Leuconostoc dextranicum* having the sucrose fermenting and dextran producing characteristics of *Leuconostoc dextranicum* NRRL-B-18242; and incubating the inoculated growth medium at a temperature of between about 10° to 50° C. to produce the dextran in depleted growth medium which has a slushy, applesauce-like appearance.

The depleted sucrose growth medium containing dextran can be treated with a water miscible solvent which is a non-solvent for the dextran to precipitate the dextran in pure form Lower alcohols containing between 1 to 6 carbon atoms, such as isopropanol, are preferred. The resulting precipitated purified dextran can be filtered from the solution The dextran can then be dried Upon rehydration of the purified dextran the gel-like structure of the dextran is lost.

The novel dextran can be used directly as it is produced in the growth medium and blended into food; however, it is preferred to dry it to a rehydratable powder for storage and shipment as described in U.S. patent application Ser. No. 68,435. Generally a food grade drying aid, preferably non-fat dry milk (NFDM), a milk derivative or other protein source is used to prepare the powder The drying aid can be incorporated into the growth medium and fermented at 15° to 35° C. with the sucrose which is preferred. The medium preferably includes 5 to 15% by weight sucrose and 4 to 15% by weight milk solids. The resulting dried product contains significant amounts of the drying aid which was desirable in order to dry the dextran. A typical fermented product contained NFDM, dextran and fructose which is a by-product of the fermentation of the sucrose along with the dextran as well as water. This fermented product produced a dried product which contained NFDM and dextran in a ratio preferably between about 2:1 to 3:1 by weight as well as fructose in an amount between about 0.5 to 1 and 1 to 1 by weight based upon the dextran produced. A flavoring can be added to the dried powder so that the dextran containing composition itself becomes the food when rehydrated, which is also described in U.S. patent application Ser. No. 68,435.

The novel dextran is useful in a liquid food as a texture modifier or improver. The novel dextran is preferably used in preferred amounts between about 0 5% and 20% of a dried powder containing non-fat dry milk or other food grade drying aids. The upper limit is the amount where the food texture is poor and the lower limit is the amount which provides the proper texture.

The novel dextran is useful in a food which is solid at refrigeration or food freezer temperatures, such as ice cream or ice milk to improve texture The dextran can be used in place of carageenan and other gums for thickening and to provide resistance to melting. The novel dextran is used in preferred amounts between about 0.5% and 20% of the dried powder containing non-fat dry milk or other food grade drying aids As with the liquid foods, the upper and lower limits are determined by the desired texture enhancement.

The preferred novel dextran is produced by *Leuconostoc dextranicum* NRRL-B-18242 This strain, which is also known as Lde3.0, has been deposited at the Northern Regional Research Laboratory in Peoria, Illinois. The strain was isolated from a food (green peas). Other strains having an ability to produce the gel-like structure of FIG. 1A in pure form can be used, particularly those strains which are genetically modified strains of *Leuconostoc dextranicum* Lde 3.0.

The culture can be stored in the growth medium or separated from the growth medium. The cultures of *Leuconostoc dextranicum* NRRL-B-18242 can be admixed with a storage stabilizing agent as is well known to those skilled in the art of preserving bacteria. The culture is preferably either lyophilized or frozen for storage prior to use. For freezing, glycerol is commonly used as a stabilizing agent. For lyophilizing, non-fat dry milk is preferably used. Preferably the frozen cultures contain at least about $10^6$ cells per ml or gram. The lyophilized cultures preferably contain between above about $10^8$ cells per gram.

Specific Description

Example 1

Isolation. Various polysaccharide producing strains were isolated from the surface of green peas which had been incubated at 24° C. for 48 hours. Potential polysaccharide-producing strains were identified by colonial morphology on Leuconostoc sucrose (LS) agar (Mayeux, J. V. and A. R. Colmer, *J. Bacteriol.* 81:1009–1011 (1961)): 1% tryptone, 0.5% yeast extract, 10% sucrose, and 2% agar by weight.

EXAMPLE 2

Growth Conditions. One isolate produced large amounts of polysaccharide in a unique form. The isolate was speciated as a *Leuconostoc dextranicum* based on the following criteria: polysaccharide production, vancomycin resistance, growth at 37° C., and non-utilization of arabinose as a carbon source.

The strain Lde 3.0, was grown in two liquid media: sucrose-salts and non-fat dry milk (NFDM)-sucrose. The sucrose-salts medium (Schwartz, R. D., and E. A. Bodie, *Appl Environ Microbiol.* 48:678–679 (1984)) consisted of 0.25% yeast extract, 0.5% $K_2HPO_4$, 0.01% $MgSO_4$, and 10% sucrose by weight. The NFDM-sucrose medium consisted of 15% NFDM and 10% sucrose by weight. The NFDM was steamed for 30 minutes at 95° C. Sucrose was autoclaved separately from other media components and added after cooling. Fermentations were performed in a Bio-Flo TM Fermenter. (New Brunswick Scientific Co.) with an agitation speed of 200 rpm at a temperature of 25° C.

*Leuconostoc dextranicum* Lde3.0 was grown in sucrose-salts medium containing 100 grams per liter of sucrose and the cultures were examined visually for exopolymer production At both 24° C. and 32° C., 100ml culture appeared highly viscous after 24 hours. Strain Lde 3.0 was also grown in 100 ml NFDM-sucrose medium with similar increases in viscosity A scale-up experiment growing the strain in a one liter fermenter in NFDM-sucrose medium yield excellent viscosity after 24 hours. The Lde3.0 culture was further scaled up to 10 liters of NFDM-sucrose. The dextran had the form shown in FIG. 1A. The dextran was spray dried The resultant powder regained excellent viscosity after rehydration, but not the form shown in FIG. 1A and was more like the dextran shown in 1B.

EXAMPLE 3

Purification of dextran produced by *L. dextranicum* Lde3.0. Dextran from *L. dextranicum* Lde3.0 was purified using a method adapted from one used to isolate xanthan gums (Cottrell, I. W., and K. S. Kang, *Dev. Ind Microbiol.* 19:117–131 (1978)). *L. dextranicum* Lde3.0 was grown for 24 hours at 32° C. in one liter sucrose-salts medium. One liter of isopropanol was added to the culture, mixed, and the resulting precipitate filtered for 48 hours. The dextran was dried in air and crushed to a powder using a mortar and pestle.

Scale-ups at ten liters and fifty gallons of NFDM-sucrose medium produced equivalent results A fine, white powder was obtained by spray-drying the NFDM-sucrose culture. This powder regained equivalent viscosity upon rehydration, but not the form shown in FIG. 1A and was more like the dextran shown in FIG. 1B. The excellent rehydration capability of the powder provided usefulness in various food products.

EXAMPLE 4

Lde3.0 was determined to be a prolific producer of dextran, more than double that produced by the best available dextran-producing strain. High levels of production were achieved at both 24° C. and 32° C. and in sucrose-salts and NFDM-sucrose media. This example shows a comparison of dextran yields from *L. dextranicum* Lde1.0 as described in U.S. patent application Ser. No. 68,435 as shown in FIG. 1B and Lde3.0 as shown in FIG. 1A.

One liter samples were obtained from fifty gallon fermenter preparations. Strains were grown in sucrose-salts medium containing 100 grams per liter of sucrose. An equal volume of isopropanol was added to each of the preparations and mixed. After several hours at 4° C., the isopropanol was decanted and fresh isopropanol was added to the precipitates. After several hours at 4° C., the isopropanol was decanted again and the precipitate was washed twice more. The precipitate was then extensively dried (air-dried and then vacuum desicated) and ground up with a mortar and pestle. The results are shown in Table 1.

TABLE 1

| Comparison of Dextran Yield vs. Lde3.0. | | |
|---|---|---|
| | Appearance | Yield/liter |
| Lde1.0 | powdery white | 25.4 g |
| Lde3.0 | powdery white | 56.0 g |

As can be seen Lde3.0 produced a much greater amount of dextran per liter of sucrose solution.

EXAMPLE 5

The dextran from *Leuconostoc dextranicum* NRRL-B-18242 was examined for polymer composition and degree of branching by C-NMR analysis. The sample was prepared as an aqueous solution. It was found to contain a mixture of polymers containing 1,6-glucopyranose with branching approximately every 11 residues and was approximately 2% fructofuranose. The dextran produced by Lde1.0 (NRRL-B-18132) was found to contain 1,6-glucopyranose with branching approximately every 20 to 30 residues with approximately 5 to 10% fructofuranose. Thus Lde3.0 exopolysaccharide contained less levan and a much higher level of branching than Lde1.0.

Use Examples

The novel dextran of Example 2 was used in various foods including ice cream, ice milks, yogurt, buttermilk, sour cream, sausage and the like. The results are shown in Examples 6 to 9. Much less dextran from Lde3.0 was required to provide the improved results as compared to dextran from conventional strains of *Leuconostoc dextranicum*.

EXAMPLE 6

Yogurt was prepared using differing concentrations of the dextran from Lde3.0 which had been prepared in sucrose-nonfat dry milk medium (10% sucrose and 15% NFDM) and spray dried to a powder. The fermented growth medium (1000 grams) contained 150 grams of NFDM, 56 grams of dextran and 44 grams of fructose by weight and the balance water which was essentially removed. This fermented product produced a dried product which contained 60% NFDM, 22.4% dextran and 17.6% fructose by weight without considering water. Yogurts were prepared with 0.06% by weight pectin (control) and 0.5% and 1.0%, respectively, by weight dextran powder. Subjective analysis of the yogurt-containing dextran versus the pectin control (0.06% by weight) demonstrated a thicker texture for the dextran powder at 0.5% by weight. Stirred yogurts were held at 4° C. for ten days and examined for wheying off. The 0.5% by weight dextran sample had much less whey present than the 0.06% by weight pectin sample. A yogurt sample containing 1.0% by weight dextran powder had almost no detectable whey at the surface.

EXAMPLE 7

This Example shows the use of the dextran powder as a thickener in milk drinks. Spray-dried dextran-milk powder from a *Leuconostoc dextranicum* Lde3.0 culture grown in nonfat dry milk-sucrose medium as in Example 6 was reconstituted to 20% (w/v) in 250 ml distilled water and blended. Ninety (90) g of frozen orange juice concentrate was added and again blended until completely mixed. The amount of solids was determined to be 21 brix using a handheld refractometer because of the orange juice concentrate.

The orange milk drink was too thick after blending. Therefore, an additional 250 ml distilled water was added along with an additional 90 g of orange juice concentrate. After blending, the amount of solids was determined to be 16 brix by refractometer. This drink was desirable in terms of flavor, texture and viscosity.

This reconstituted dextran-milk powder is useful at 10% w/v in flavored milk drinks as a thickener conferring body.

EXAMPLE 8

This Example shows the use of the dextran powder as an ingredient in ice cream. Spray-dried dextran-milk powder from *Leuconostoc dextranicum* Lde3.0 culture grown in nonfat dry milk-sucrose medium as in Example 6 was reconstituted to 16 brix (20% w/v) in distilled water as determined using a handheld refractometer. One cup of this reconstituted powder was added to one half cup sucrose and mixed with light heating until dissolved. One cup of whipping cream, one cup of 2% low fat milk and one tablespoon of vanilla were added and all ingredients were then mixed together and processed in an ice cream freezer.

The ice cream product with the dextran displayed a light, fluffy texture and excellent consistency. The spray-dried dextran-milk powder is useful for ice cream. The recipe eliminates half the whipping cream from the conventional recipe resulting in fewer calories and less fat in the final product.

EXAMPLE 9

This example shows the use of dextran powder as an ingredient in salad dressing. Spray-dried dextran-milk powder from *Leuconostoc dextranicum* Lde3.0 culture grown in nonfat dry milk-sucrose medium as in Example 6 was reconstituted to 15% by weight solids in distilled water to a final volume of 400 ml. Twenty-five percent (25%) (vol/vol) reconstituted lemon juice and 4% (vol/vol) olive oil were added along with the following seasonings: oregano—1.0 g, garlic powder—2.0 g, and seasoning salt—2.0 g. The ingredients were mixed in a blender until evenly dispersed.

The salad dressing made from the dextran-milk powder exhibited good viscosity and coating capability. The viscosity increased upon storage at 4° C. The spices remained well suspended after storage and the flavor was good with little residual sweetness. The final pH was 4.01 which is desirable. It was concluded that the spray-dried dextran powder was useful as a thickening agent for salad dressings.

EXAMPLE 10

It was found that the slushy, applesauce-like appearance particulate, gel-like structured dextran product obtained when *Leuconostoc dextranicum* Lde3.0 is grown in sucrose-salts medium of Example 2, was stable at room temperatures for 12 months without microbial growth. The container was covered with foil and frequently opened to the atmosphere. The novel dextran was antimicrobial in spite of its high $A_\omega$ which was 0.987.

It is intended that the foregoing description be only illustrative of the present invention and that the present invention be limited only by the hereinafter appended claims.

We claim:
1. A culture which comprises in admixture:
   (a) biologically pure *Leuconostoc dextranicum* NRRL-B-18242 grown in an aqueous growth medium containing sucrose until the sucrose is substantially depleted; and
   (b) a synthetic growth medium for the *Leuconostoc dextranicum*.
2. The culture of claim 1 in freeze dried form.
3. The culture of claim 1 in frozen form.
4. The culture of claim 1 wherein the culture contains at least $10^6$ cells per gram.
5. A biologically pure culture of *Leuconostoc dextranicum* NRRL-B-18242.

* * * * *

UNITED STATES PATENT AND TRADEMARK OFFICE
CERTIFICATE OF CORRECTION

PATENT NO.   : 5,223,431

DATED        : June 29, 1993

INVENTOR(S)  : Michael J. Pucci and Blair S. Kunka

Page 1 of 2

It is certified that error appears in the above—identified patent and that said Letters Patent is hereby corrected as shown below:

Column 1, line 10, "4,855,14" should be --4,855,149--.

Column 1, line 54, a period --.-- should be inserted after "study" and before "First".

Column 2, line 7, a period --.-- should be inserted after "foods" and before "Further".

Column 2, line 66, a period --.-- should be inserted after "form" and before "Lower".

Column 3, line 1, a period --.-- should be inserted after "solution" and before "The".

Column 3, line 2, a period --.-- should be inserted after "dried" and before "Upon".

Column 3, line 11, a period --.-- should be inserted after "powder" and before "The".

Column 3, line 33, "05%" should be --0.5%--.

Column 3, line 40, a period --.-- should be inserted after "texture" and before "The".

UNITED STATES PATENT AND TRADEMARK OFFICE
CERTIFICATE OF CORRECTION

PATENT NO. : 5,223,431

DATED : June 29, 1993

INVENTOR(S) : Michael J. Pucci and Blair S. Kunka

It is certified that error appears in the above—identified patent and that said Letters Patent is hereby corrected as shown below:

Column 3, line 45, a period --.-- should be inserted after "aids" and before "As".

Column 3, line 49, a period --.-- should be inserted after "NRRL-B-18242".

Column 4, line 37, a period --.-- should be inserted after "production" and before "At".

Column 4, line 40, a period --.-- should be inserted after "viscosity" and before "A".

Column 4, line 46, a period --.-- should be inserted after "dried" and before "The".

Column 4, line 62, a period --.-- should be inserted after "results" and before "A".

Signed and Sealed this

First Day of February, 1994

Attest:

BRUCE LEHMAN

*Attesting Officer*     *Commissioner of Patents and Trademarks*